(12) United States Patent
Bobrow et al.

(10) Patent No.: US 6,399,299 B1
(45) Date of Patent: Jun. 4, 2002

(54) AMPLIFIED ARRAY ANALYSIS SYSTEM

(75) Inventors: Mark Norman Bobrow, Lexington; Karl Edwin Adler, Newburyport, both of MA (US)

(73) Assignee: PerkinElmer Life Sciences, Inc., Boston, MA (US)

( * ) Notice: Subject to any disclaimer, the term of this patent is extended or adjusted under 35 U.S.C. 154(b) by 0 days.

(21) Appl. No.: 09/430,429

(22) Filed: Oct. 29, 1999

Related U.S. Application Data

(60) Provisional application No. 60/106,653, filed on Nov. 2, 1998.

(51) Int. Cl.$^7$ .............................. C12Q 1/68; C12M 1/36; C07H 21/04; G01N 15/06
(52) U.S. Cl. ...................... 435/6; 435/287.2; 435/288.7; 536/24.3; 422/50; 422/68.1
(58) Field of Search ...................... 435/6, 287.2, 288.7; 536/24.3; 422/50, 68.1

(56) References Cited

U.S. PATENT DOCUMENTS

| | | | |
|---|---|---|---|
| 5,143,854 A | 9/1992 | Pirrung et al. | 436/518 |
| 5,196,306 A | 3/1993 | Bobrow et al. | 435/7.9 |
| 5,405,783 A | 4/1995 | Pirrung et al. | 436/518 |
| 5,445,934 A | 8/1995 | Fodor et al. | 435/6 |
| 5,489,678 A | 2/1996 | Fodor et al. | 536/22.1 |
| 5,525,464 A | 6/1996 | Drmanac et al. | 435/6 |
| 5,583,001 A * | 12/1996 | Bobrow et al. | 435/7.5 |
| 5,700,637 A | 12/1997 | Southern | 435/6 |
| 5,731,158 A | 3/1998 | Bobrow et al. | 435/7.5 |
| 5,744,305 A | 4/1998 | Fodor et al. | 435/6 |
| 5,800,992 A | 9/1998 | Fodor et al. | 435/6 |
| 5,871,928 A | 2/1999 | Fodor et al. | 435/6 |

* cited by examiner

*Primary Examiner*—Stephanie W. Zitomer
*Assistant Examiner*—B J Forman
(74) *Attorney, Agent, or Firm*—Gifford, Krass, Groh, Sprinkle, Anderson & Citkowski, P.C.

(57) ABSTRACT

The present invention concerns an array-based analytical system and method having an enhanced sensitivity which allows for simple and rapid analysis of relative unmodified samples which comprises an analytical system of the type having a plurality of different first members of a specific binding pair affixed in an array thereupon, a mixture including at least one second member of a specific binding pair capable of binding to one of the first members so as to form a specific binding pair which is affixed to the support member, and a reporter system that produces a detectable signal indicative of the presence of the specific binding pair on the support member and wherein the reporter system includes an amplified reporter system that is independent of layering.

5 Claims, 3 Drawing Sheets

(1 of 3 Drawing Sheet(s) Filed in Color)

US 6,399,299 B1

AMPLIFIED ARRAY ANALYSIS SYSTEM

RELATED APPLICATION

This application claims priority of U.S. Provisional Application Serial No. 60/106,653 filed Nov. 2, 1998.

FIELD OF THE INVENTION

This invention relates to analytical systems wherein arrays of at least one material such as oligonucleotides, DNA and/or RNA and/or fragments thereof, peptides, protein fragments, cell fragments, cells and tissues is disposed on a support member and is contacted with a mixture which may or may not include a material which includes binding pair members which bind to at least one of the materials comprising the array. Most specifically, the invention relates to analytical systems of this type which further include an amplified reporter system that do not depend on layering.

BACKGROUND OF THE INVENTION

Many analytical techniques and systems are based upon the ability of various materials to form a specific binding pair. As used herein, a specific binding pair is a system wherein the two components share an affinity for each other so as to cause one of the components contained in a mixture of materials to bind to the other upon contact. Either or both components of a specific binding pair may be organic or inorganic. Some examples of specific binding pairs are antibodies and antigens, nucleic materials such as DNA, RNA and fragments thereof, free nucleotides, metallic moieties and nucleic acids or proteins, biotin and avidin, folic acid-folate binding protein, sulfhydryls and sulfhydryl reactive groups such as maleimides and haloacetyl derivatives, amines and amine reactive groups such as succinimidyl esters and isothiocyanates, etc.

Typical assays based upon the formation of specific binding pairs include a reporter system which provides a detectable signal indicative of the formation of a specific binding pair. For example, one of the members of the pair can be provided with a label which can comprise a fluorescent material, a radioactive material, any other signaling moiety, or a material which is further reactive with another species to form a colored complex or some other such detectable reaction product. The reporter system in these types of assays is commonly referred to as a layered-type system wherein successive layers of reagents such as labeled antibodies or nucleic acid probes are applied one after another in successive manipulation to generate a detectable signal.

Recently, a number of technologies have been developed which enable the production of very large arrays comprised of one or more differing materials such as oligonucleotides, DNA and/or RNA and/or fragments thereof, peptides, protein fragments, cell fragments, cells and tissues disposed upon a support body. The various members comprising the array are each capable of forming a unique, specific binding pair with their appropriate counterpart, and such arrays have great utility for rapidly screening mixtures for the presence or absence of a large number of materials. Techniques for the fabrication of such arrays will be found, for example, in U.S. Pat. No. 5,744,305; 5,489,678; 5,445,934; 5,405,783; and 5,143,854, the disclosures of which are incorporated herein by reference. The formation of specific binding pairs is detected in such arrays by utilizing conventional reporter technology, of the type described hereinabove.

There is often a need to increase the sensitivity of such assays. For example, in many instances, species will be present in the mixture at very low concentrations; hence, the detectable signal produced thereby will be very weak. Target amplification techniques, such as polymerase chain reaction (PCR) amplification may be applied to a sample containing nucleic materials so as to increase the concentration of these materials. However, PCR reaction, can be time consuming and difficult to implement. Therefore, it will be appreciated that there is a need for an array-based analytical system and method having an enhanced sensitivity which does not require such complex sample preparation or manipulation. The enhanced sensitivity of an assay of this type would allow for rapid and simple analysis of relatively unmodified biological fluids, preparations and the like. As will be described in detail hereinbelow, the present invention incorporates an amplification system into an array-based analysis. The system of the present invention may be utilized for the analysis of materials such as oligonucleotides, DNA and/or RNA and/or fragments thereof, peptides, protein fragments, cell fragments, cells and tissues.

SUMMARY OF THE INVENTION

The present invention provides a method for enhancing the sensitivity of array-based analytical assay systems which comprises a support member having at least one different first member of a specific binding pair affixed in an array thereupon, a mixture which may include at least one second member of a specific binding pair capable of binding to one of the first members so as to form a specific binding pair which is affixed to the support member, and a reporter system that produces a detectable signal indicative of the presence or absence of the specific binding pair on the support member wherein the reporter system comprises an amplified reporter system that is independent of layering.

BRIEF DESCRIPTION OF THE FIGURES

This application contains at least one photograph executed in color. Copies of this application with color photographs will be provided by the U.S. Patent and Trademark Office upon request and payment of the necessary fee.

Other advantages of the present invention will be readily appreciated as the same becomes better understood by reference to the following detailed description when considered in connection with the accompanying drawings wherein.

DETAILED DESCRIPTION OF THE INVENTION

In accord with the present invention, an array-based binding assay incorporates an amplified reporter system utilized for the analysis of various materials including oligonucleotides, DNA and/or RNA and/or fragments thereof, peptides, protein fragments, cell fragments, cells and/or tissues. As used herein, an amplified reporter system means a system, in which the formation of one specific binding pair will give rise to a multitude of reporter species. This is in contrast to a nonamplified system such as a system wherein a fluorescently tagged antibody reacts with an appropriate antigen to form a specific binding pair which can include fluorescent tags or labels thereupon without generating any signal amplification from the formation of the specific binding pair.

One particularly preferred group of amplified reporter systems comprises enzymatically amplified reporter systems with catalyzed reporter deposition (CARD) being one particularly preferred amplification system. CARD amplification is a novel method of signal amplification which is disclosed in U.S. Pat. 5,731,158; 5,583,001 and 5,196,306, the disclosures of which are incorporated herein by reference. The method uses an analyte dependent enzyme activation system (ADEAS) to catalyze the deposition of reporter or hapten groups (labels) onto the solid phase of an assay support. These enzymatically deposited labels are detected directly or indirectly, which results in signal amplification and improved detection limits.

Figure 1:
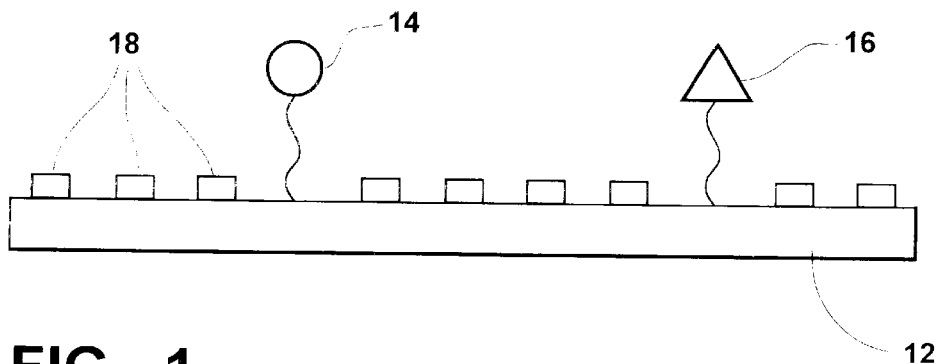
FIG. 1 is a schematic illustration of a catalyzed reporter deposition system in accordance with the present invention.

Operation of one catalyzed reporter deposition system is shown schematically in FIGS. 1–5. FIG. 1 depicts a support member 12 having an array of first members of a specific binding pair supported thereupon. As shown in FIG. 1, two members of the array 14 and 16 are depicted. As discussed above, these members can comprise materials such as oligonucleotides, DNA and/or RNA and/or fragments thereof, peptides, protein fragments, cell fragments, cells and tissues and each is capable of binding to a specific material so as to form a specific binding pair. In a typical assay, the support member 12 may be polymeric or glass and may be in the form or shape of any solid or porous support, and it will include a number of receptor sites 18 thereupon. These receptor sites 18 function to bind an activated, labeled conjugate, as will be described hereinbelow. The receptor sites 18 may comprise chemically active sites, such as phenolic sites normally present on the support member 12, or they may comprise a material separately added to the support, such as a proteinaceous material, a phenolic based material, or any other such compound capable of interacting with the activated conjugate, as will be described hereinbelow, or the support surface itself may be chemically reactive.

Figure 2:
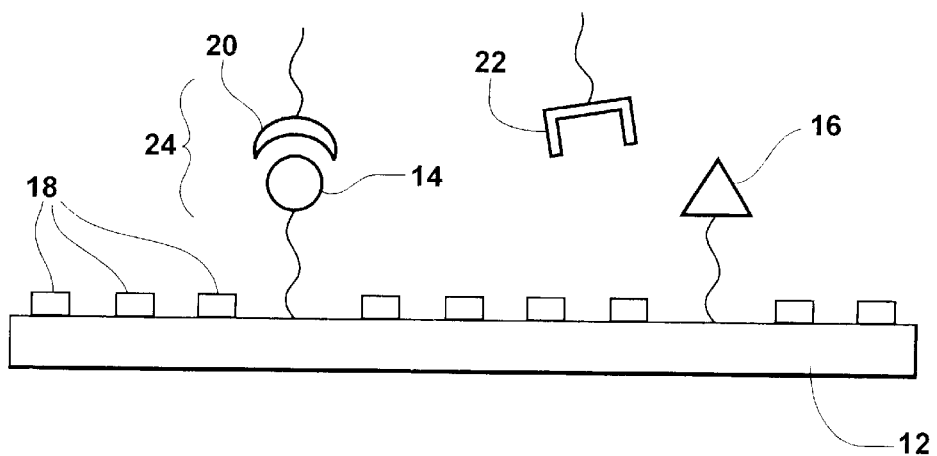
FIG. 2 is a schematic illustration of a further stage in the catalyzed reporter deposition system in accordance with the present invention.

FIG. 2 depicts a further stage in the use of the analytical system. As shown therein, the array is contacted with a mixture which may include one or more second members of a specific binding pair, capable of binding to at least one of the immobilized first members on the support 12. As specifically shown in FIG. 2, the mixture includes two different second members 20, 22. As illustrated, the second member 20 has bound to the immobilized first member 14 to form a specific binding pair 24. The other second member 22 is not capable of binding to either of the first members 14, 16, and does not form a specific binding pair, and in a subsequent step is washed away or otherwise removed from the region of the support member 12.

Figure 3:
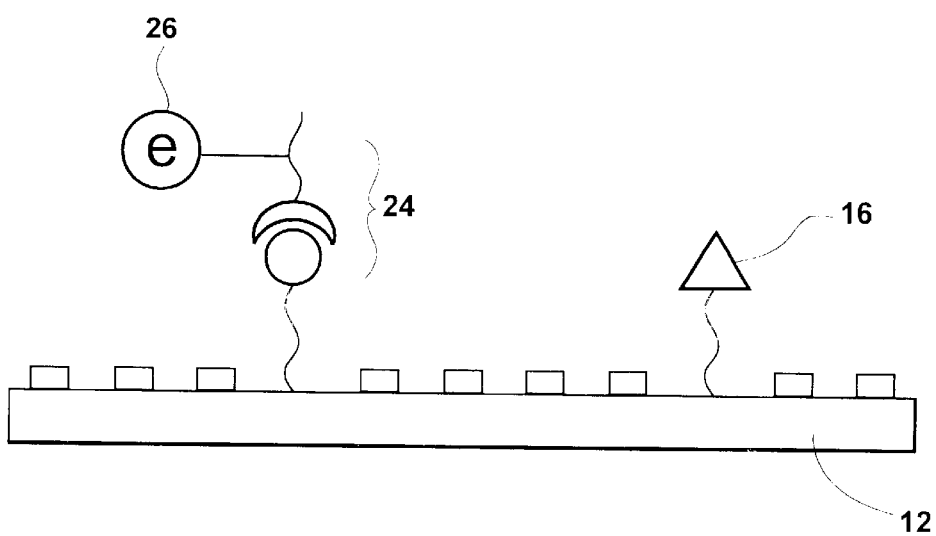
FIG. 3 is a further schematic illustration of a stage of the catalyzed reporter deposition system in accordance with the present invention.

Referring now to FIG. 3, there is shown a further step in the method. As shown therein, an enzyme 26 is coupled to the specific binding pair 24. While the Figures imply that the enzyme 26 is joined to the specific binding pair 24 after the specific binding pair is formed, the methodology of the present invention does not require this sequence of events. In some instances, the enzyme 26 may be coupled to the second member 20 prior to the formation of the binding pair, while in other instances, the enzyme 26 may be coupled after formation of the specific binding pair. Coupling can be accomplished by specific or nonspecific binding reactions. In some particular instances, the enzyme itself will be the second member of the specific binding pair, in which case, formation of the specific binding pair will inherently incorporate the enzyme. In any instance, the net result of the foregoing is that an enzyme 26 will be immobilized upon the support member 12 only at those locations in the matrix at which a specific binding pair is formed. The enzyme, in one specific embodiment, comprises horseradish peroxidase (HRP), although other enzymes may be utilized in other embodiments of the invention.

Figure 4:
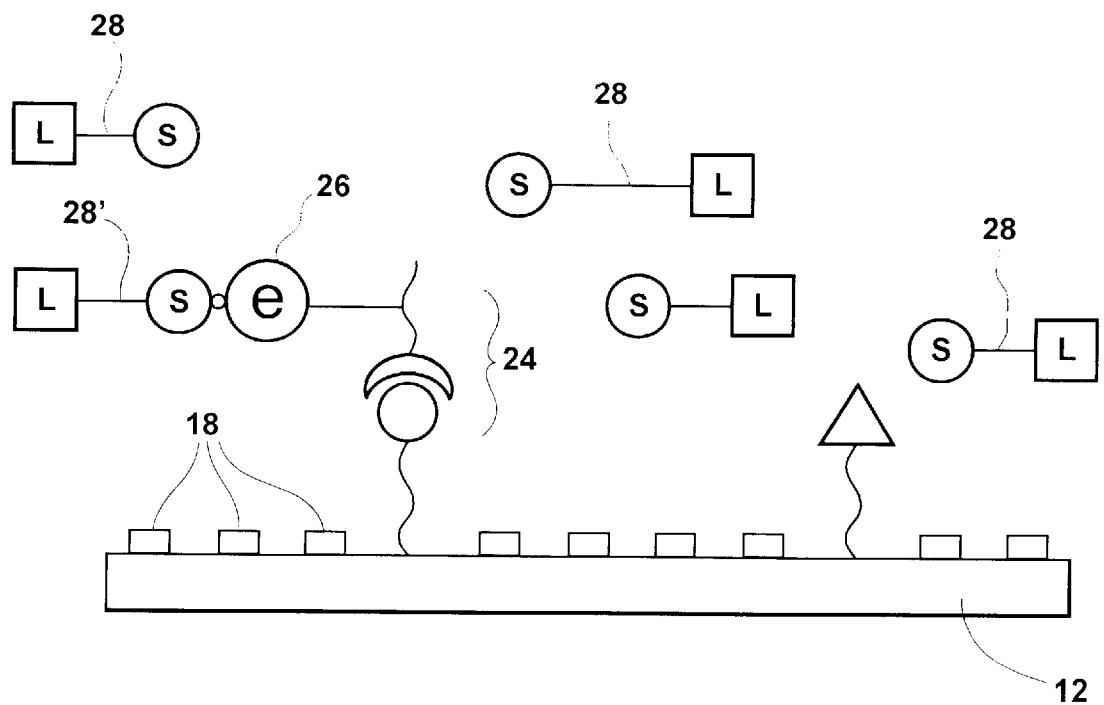
FIG. 4 is a further schematic illustration of a stage of the catalyzed reporter deposition system in accordance with the present invention.
Figure 5:
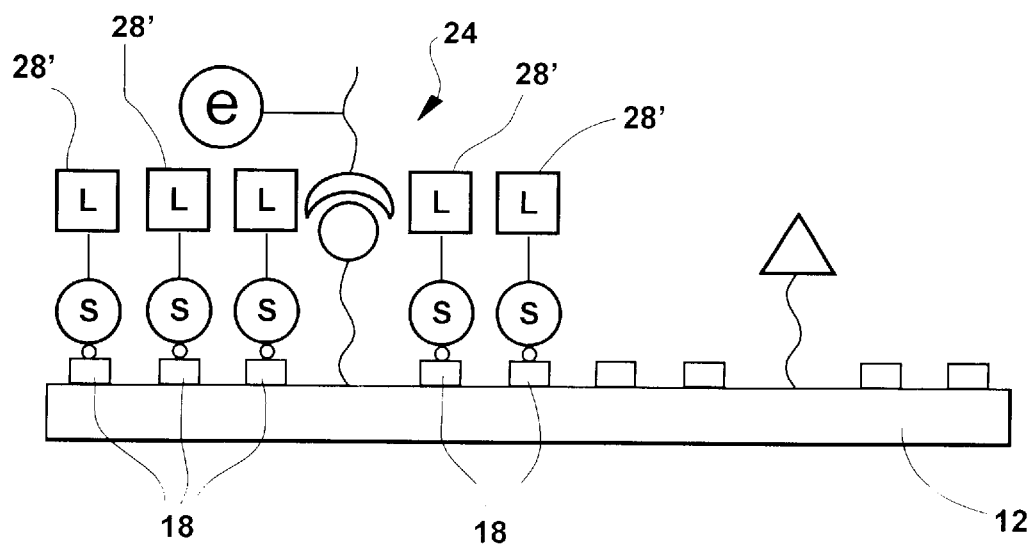
FIG. 5 is a further schematic illustration of a stage of the catalyzed reporter deposition system in accordance with the present invention.

Referring now to FIG. 4, there is shown a further stage in the operation of the analytical system of the present invention wherein the support member 12 having the specific binding pair 24 and associated enzyme 26 immobilized thereupon, is contacted with a labeled conjugate 28. The labeled conjugate 28 includes a substrate (S) for the enzyme 26, and a label (L). The substrate is a material which is activatable by the enzyme so as to cause it to bind to the receptor sites 18 on the support member 12. The receptor sites 18 may be reactive components of the support member 12 or may be added to the support member 12. The label can be any detectable label, such as a fluorescently detectable label, a hapten (e.g. biotin), a radioactive label, or a chemically reactive, color forming label or any other signaling moiety. As will be seen from FIG. 4, the enzyme 26 creates an activated conjugate 28', and as seen in FIG. 5, this activated conjugate 28' binds to the receptor sites 18 in the region of the specific binding pair 24. The unactivated conjugate 28 is not capable of binding to the receptor sites 18; hence, the label is displayed only proximate the specific binding pair 24. As noted from FIG. 5, the formation of one specific binding pair 24 catalyzes the deposition of a number of labeled conjugates, thereby providing an amplified reporter system.

The methodology of the present invention may be implemented in accord with various array-based analyses of the type shown in the prior art including both layered and non-layered assays and incorporated hereinabove by reference. Specific chemistries for the catalysts, supports, substrates, labels and members of the specific binding pair will depend upon the exact nature and purpose of the assays, which, in view of the teaching presented herein and in the patents referred to herein, will be readily apparent to one of skill in the art.

Example

Comparison OF Direct AND Amplified Array Analysis

For direct detection, cyanine 5 labeled cDNA was prepared from 100μg and 4μg Jurkat total RNA using the MICROMAX Direct Reagent Kit (NEN Life Science Products, Boston, Mass.). The cyanine 5 labeled cDNA was hybridized to Practice Slides (MICROMAX Human cDNA Microarray System I, NEN Life Science Products, Boston, MA) a microarray system for differential gene expression analysis according to MICROMAX Human cDNA System I-Direct (NEN Life Science Products, Boston, Mass.) kit directions.

For amplified analysis, biotin labeled cDNA was prepared from 4μg Jurkat total RNA using the MICROMAX Human cDNA Microarray System I kit reagents and protocols. Hybridization to Practice Slides and amplified detection using streptavidin-HRP and cyanine 5 tyramide were according to the MICROMAX Human cDNA Microarray System I kit directions.

Slides were scanned on a GSI Lumonics ScanArray 5000 (Watertown, Mass.) scanner.

Figure 6A:
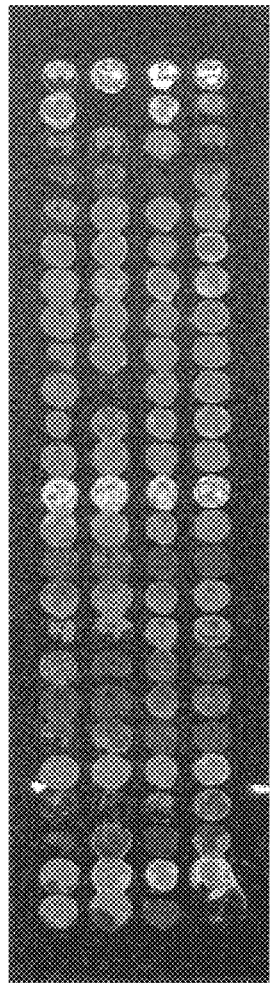
FIGS. 6A–C are reproductions illustrating a comparison of direct and amplified array analysis wherein (A) illustrates the results for direct analysis using 100$\mu$g total RNA, (B) illustrates the results obtained for direct analysis using 4$\mu$g total RNA, and (C) illustrates the results for amplified analysis using 4$\mu$g RNA.
Figure 6B:
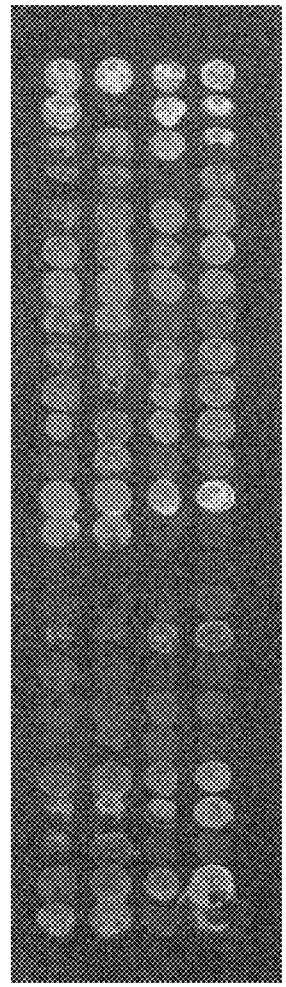
Figure 6C:
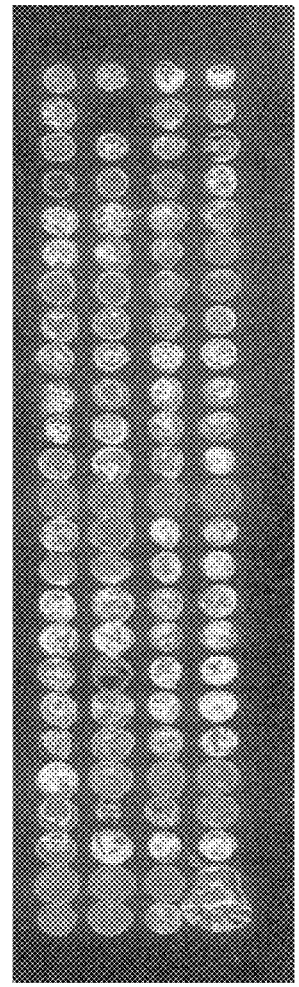

The results for direct analysis using 100μg total RNA are shown in FIG. 6A. FIG. 6B shows the results obtained for direct analysis using 4μg total RNA. The results for amplified analysis using 4μg total RNA is shown in FIG. 6C. The loss of signal going from 100μg to 4μg of total RNA for direct analysis indicates that there is insufficient material available for adequate analysis. A greater amounts of cells or tissue mass is required for the direct method. The signal for the amplified analysis using 4μg of total RNA is greater than that using 100μg for direct analysis, allowing for much greater flexibility in analyzing small amounts of tissues or cells.

The foregoing drawings, discussion and description are illustrative of the general principles of the present invention, and some specific embodiments thereof, but are not meant to be limitations upon the practice of the present invention, since numerous modifications and variations will be readily apparent to one of skill in the art. It is the following claims, including all equivalents, which define the scope of the invention.

What is claimed is:

1. An analytical system comprising:

a support member having a plurality of chemically active phenolic or proteinaceous receptor sites hereupon;

an array of different first members of a specific binding pair disposed on said support, said first members being selected from the group consisting of DNA, cDNA, RNA, oligonucleotides, and combinations thereof, said first members each being capable of binding to a complementary second member of said specific binding pail, whereby when said array is contacted with a plurality of analyte complementary second members, a plurality of specific binding pairs will be formed on said support;

a peroxidase enzyme;

a coupling agent operative to couple said enzyme to said specific binding pairs;and a conjugate of a labelling agent and a substituted phenol substrate for said enzyme, said substrate being activatable by said enzyme so as to cause said substrate to bind to one of said chemically active receptor sites whereby said substrate and said labelling agent are immobilized upon said support.

2. An analytical system as in claim 1, wherein said coupling agent is operative to couple said enzyme to the second member of said specific binding pair.

3. An analytical system as in claim 1, wherein said peroxidase enzyme comprises horseradish peroxidase.

4. An analytical system as in claim 1, wherein said substituted phenol substrate comprises tyramine.

5. An analytical system as in claim 1, wherein said labelling agent comprises a fluorescent cyanine dye.

* * * * *